(12) United States Patent
Schroder

(10) Patent No.: US 8,450,533 B2
(45) Date of Patent: May 28, 2013

(54) CYCLOPROPANATION PROCESS

(75) Inventor: Fridtjof Schroder, Hettlingen (CH)

(73) Assignee: Givaudan SA, Vernier (CH)

( * ) Notice: Subject to any disclaimer, the term of this patent is extended or adjusted under 35 U.S.C. 154(b) by 590 days.

(21) Appl. No.: 12/673,901

(22) PCT Filed: Aug. 19, 2008

(86) PCT No.: PCT/CH2008/000352
§ 371 (c)(1),
(2), (4) Date: Feb. 17, 2010

(87) PCT Pub. No.: WO2009/023980
PCT Pub. Date: Feb. 26, 2009

(65) Prior Publication Data
US 2011/0124924 A1    May 26, 2011

(30) Foreign Application Priority Data
Aug. 21, 2007 (GB) .................... 0716232.4

(51) Int. Cl.
*C07C 31/133* (2006.01)
*C07C 27/00* (2006.01)

(52) U.S. Cl.
CPC ...................................... *C07C 27/00* (2013.01)
USPC ............ 568/700; 568/816; 568/817; 568/819

(58) Field of Classification Search
USPC ................................. 568/700, 816, 819, 817
See application file for complete search history.

(56) References Cited

U.S. PATENT DOCUMENTS
4,973,767 A * 11/1990 Crowley et al. ............... 568/807

FOREIGN PATENT DOCUMENTS

| EP | 1702911 A1 | 9/2006 |
|---|---|---|
| GB | 1447473 A | 8/1976 |
| WO | 2006066436 A | 6/2006 |
| WO | 2007015111 A | 2/2007 |
| WO | 2007117462 A | 10/2007 |

OTHER PUBLICATIONS

Whitmore et al; Journal of American Chemical Society, 1933, 55(4), 1559-1567.*
XP002508329, Friedrich et al., Zince Dust-Cuprous Chloride Promoted Cyclopropanations of Allylic Alcohols Using Ethylidene Iodide, Journal of Organic Chemistry, vol. 47, No. 9, 1982, pp. 1615-1618.
XP004111211, C. Bolm et al., Magnesium Promoted Cyclopropanation Reactions of Allylic Alcohols, Tetrahedron Letters, Elsevier, Amsterdam, vol. 38, No. 42, pp. 7349-7352, Oct. 1997.
XP002508330, Durandetti et al., Electrochemical Cyclopropanation of Alkenes Using Dibromomethane and Zinc in CH2C12/DMF Mixture, Journal of Organic Chemistry, vol. 56, pp. 3255-3258, 1991.
XP002508331, Friedrich et al., Acetyl Chloride Promoted Cycloprapanations of Alkenes with Dibromomethane Using Zinc Dust and Copper (I) Chloride in Ether, Journal of Organic Chemistry, vol. 55, No. 8, pp. 2491-2494, 1990.
XP002508328. Brinker et al., Dihalocarbene Insertion Reactions Into C-H Bonds of Compounds Containing Small Rings: Mechanism and Regio-and Stereoselectivities, Journal of Organic Chemistry, vol. 72, pp. 8434-8451, p. 8439, 2007.
Bolm et al., Tetrahedron Letters, vol. 38(42), pp. 7349-7352, 19973.

* cited by examiner

*Primary Examiner* — Johann R Richter
*Assistant Examiner* — Pancham Bakshi
(74) *Attorney, Agent, or Firm* — Norris mcLaughlin & Marcus PA

(57) ABSTRACT

A method for the preparation of cyclopropyl carbinols by cyclopropanation of unsaturated alcoholates, utilizing a reagent system selected from (A) magnesium metal and dibromomethane, and (B) dibromomethane and a tertiary Grignard reagent, the reaction being carried out in the presence of an ether solvent.
The process is useful, for example, for the preparation of ingredients for the flavor and fragrance industry.

6 Claims, No Drawings

CYCLOPROPANATION PROCESS

This is an application filed under 35 USC 371 of PCT/CH2008/000352.

This invention relates to a process of preparing cyclopropane carbinols from allylic alcoholates.

Cyclopropane carbinols are desirable compounds for some industries, for example, the fragrance and flavour industries. There is therefore an interest in their efficient production. One possible method is by the cyclopropanation of allylic alcohols. (In the following description, the term "allylic alcohol" includes homoallylic alcohols, and the term "cyclopropane carbinol" includes 2-cyclopropyl-ethanols).

Allylic alcohols have been cyclopropanated by a variety of methods, which are described in recent reviews, for example, those by A. B. Charette, A. Beauchemin, *Organic Reactions* 58, 1-416, 2001, and by M. Regitz, Carbenoids, *Methoden der organischen Chemie*, Houben-Weyl, (Georg Thieme Verlag Stuttgart—New York, Vol. E19b, pp 179-212, 1989). The reaction is believed to proceed via the formation of an allylic alcoholate and a carbenoide.

The most convenient and efficient of these methods are those using a metal or a metal mixture (Zn, Cu, Sm and Hg) or an organometallic reagent ($ZnEt_2$, $AlEt_3$ or iPrMgCl), together with an iodinated carbenoide precursor ($CH_2I_2$ or $ClCH_2I$). From these reagents, there are formed carbenoides, intermediates of the type X-M-$CH_2$—X (M=metal, X=halide). In the presence of an allylic alcohol or allylic alcoholate, the $CH_2$-group of the carbenoide is directed intramolecularly on to the allylic double bond and effects cyclopropanation (a recent review describing this mechanism is one by A. H. Hoveyda, D. A. Evans, G. C. Fu *Chem. Rev.* 93, 1307-1370, 1993).

It would be more efficient to use dibromomethane rather than iodinated dihalomethanes because it is less expensive, more stable and avoids undesired iodine wastes. However, dibromomethane is less reactive than diiodomethane in this reaction. This can be overcome by activating with a zinc-copper couple, followed by cyclopropanation by means of ultrasound (E. C. Friedrich, J. M. Domek, R. Y. Pong, *J. Org. Chem.* 50, 4640-4642, 1985) or with additives such as copper halides and acetyl halides (E. C. Friedrich, F. Niyati-Shirkhodaee, *J. Org. Chem.* 56, 2202-2205, 1991). However, both of these methods result in the generation of environmentally-unfriendly zinc- and copper-based wastes.

It has now been found that it is possible efficiently to cyclopropanate allylic alcoholates with dibromomethane under Grignard or Barbier conditions conveniently between 0° C. and 70° C. There is therefore provided a method for the preparation of a compound of the formula I:

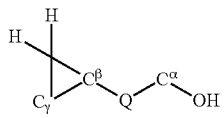

comprising the generation of an alcoholate of the formula II

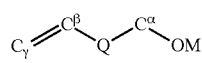

and the subsequent cyclopropanation of this alcoholate with a reagent system selected from (A) magnesium metal and dibromomethane, and (B) dibromomethane and a tertiary Grignard reagent, the reaction being carried out in the presence of an ether solvent, $C^\alpha$, $C^\beta$, $C^\gamma$ and Q being selected according to the possibilities (a) and (b):

(a) $C^\alpha$, $C^\beta$, $C^\gamma$ represent carbon atoms that may be protonated or substituted with up to a total of 5 substituents for all three carbon atoms, the substituents being selected from the group consisting of alkyl, alkenyl, cycloalkyl and cycloalkenyl groups; and Q represents a moiety selected from (i) a saturated or unsaturated carbon chain having from 1-6 carbon atoms, preferably 1 carbon atom, which carbon atoms are protonated or substituted, the substituents being selected from any of those of $C^\alpha$, $C^\beta$, $C^\gamma$; and (ii) a single covalent bond joining $C^\alpha$ and $C^\beta$; and;

(b) $C^\alpha$, $C^\beta$, $C^\gamma$ and all or part of Q together form a cycloalkyl or cycloalkenyl ring; and (c) M is an alkali metal, an alkaline earth metal, or an alkaline earth metal monohalide Any substituents that may be present on $C^\alpha$, $C^\beta$, $C^\gamma$ and Q may themselves be substituted with functional groups, such as (but not limited to) alcohols, ethers, amines, alkyl amines, alkenes, alkynes, cycloalkanes and cycloalkenes.

The alcoholate of Formula II may be prepared from many precursors and by many methods. The preparation of such alcoholates is well known to the art, and will not be further described in detail here, but the general scheme specific for allyl alcoholates shown below (with the substituents R, $R^\alpha$, $R^\beta$, $R^\gamma$ and M=Na, Li or MgX (where X=halide) as hereinabove described) illustrates some of the possibilities. It is to be borne in mind that this scheme is for purposes of illustration only and is not to be construed to be in any way limiting on the scope of the method.

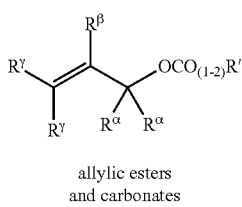

allylic esters and carbonates

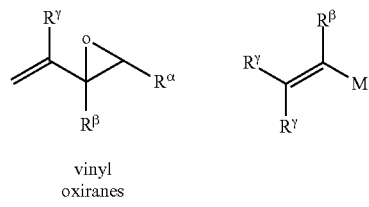

vinyl oxiranes aldehydes or ketones

-continued

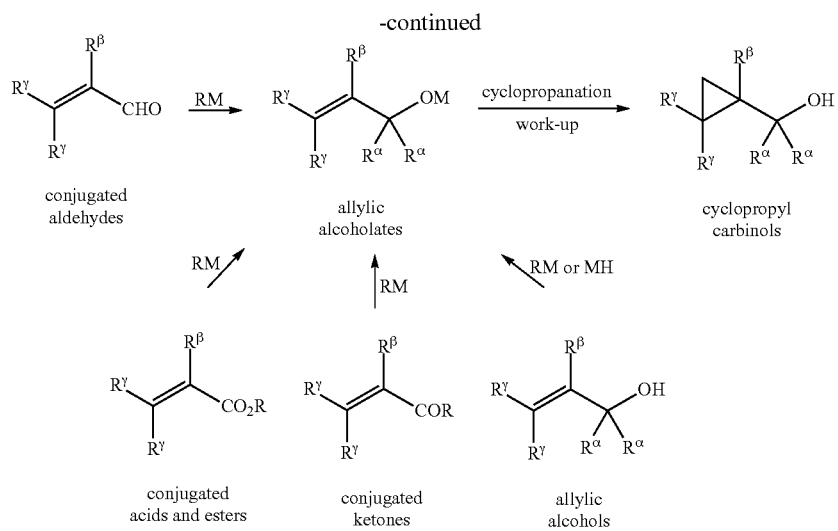

Without restricting the scope of the invention in any way, it is believed that, under the conditions hereinabove defined, carbenoides of the type X—Mg—CH$_2$—Br are formed from the reagent systems, and that the CH$_2$ group of this carbenoide is delivered on to the double bond of the compound of Formula II, giving the cyclopropane carbinol. In this carbenoide, X is nearly always Cl.

This is surprising as carbenoides derived from dibromomethane and organomagnesium reagents have been reported as being unstable above −50° C. (J. Villiéras, *Comptes Rendues* 261, 4137-4138, 1965), and only recently a low conversion (19%) of an allylic alcohol to the corresponding cyclopropane carbinol has been observed (C. Bolm, D. Pupowicz, *Tetrahedron Lett.* 38, 7349-7352, 1997) under such conditions (isopropyl magnesium chloride, dibromomethane, −70° C., 3 days).

The reaction is carried out in the presence of an ether solvent. In a particular embodiment, the ether solvent (which may be a single solvent or a mixture of such solvents) is present from the beginning, but in a further embodiment, it is added at the same time as, or immediately prior to, the addition of the reagent system. The ether solvent may be any ether known to be useful as a solvent, particular examples including tetrahydrofuran (THF), diethyl ether and methyl t-butyl ether.

In a particular embodiment, the reagent system is used with allylic alcohols, including homoallylic alcohols, i.e, alcohols in which, in the Formula II above, Q is respectively a single bond and a single carbon atom. There is therefore also provided a method of preparation of a cyclopropyl carbinol, comprising the generation of an allylic alcoholate and the subsequent cyclopropanation of this allylic alcoholate with a reagent system selected from (A) magnesium metal and dibromomethane (hereinafter "System A"), and (B) dibromomethane and a tertiary Grignard reagent (hereinafter "System B"), the reaction being carried out in the presence of an ether solvent. The magnesium metal is usually in the form of turnings or powder.

In the embodiment of this process utilising System B, the tertiary Grignard reagent may be a commercially-available material or one prepared prior to its use in the process. The Grignard reagent is of the formula R$_3$CMgX, the moieties R being selected from C1-C7 alkyl, such that the number of carbon atoms in R$_3$C is from 4-22. In addition, one or more of the moieties R may, with the C, form part of at least one ring system. In particular embodiments, R$_3$C is tert-butyl or tert-amyl, and the halide X is particularly Cl.

It should be noted that, while both Systems A and B work in all cases, there is a difference in efficacy, depending on the nature of the compound of Formula II. For example, in the case of Q having two or more carbon atoms (that is, not being an allylic or homoallylic alcoholate), System A is more efficient than System B in terms of conversion of double bonds to cyclopropane rings when this double bond is more than one carbon atom removed from the α-C atom of Formula II (i.e., when Q is at least 2).

In the case where Q represents a single bond, the allylic alcohols are preferably disubstituted in their α,γ- or β,γ-positions, trisubstituted in their α,β,γ-positions, tetrasubstituted in α,β,γ,γ-positions or pentasubstituted in their α,α,β,γ,γ-positions. Fewer substituents and/or substituents in other positions are also possible but they give a lower percentage conversion (that is, more reagent is needed for complete conversion).

Particular examples of alcohols that undergo the cyclopropanation reaction using System A, including remote alkenes in the same molecule include those with the following structures:

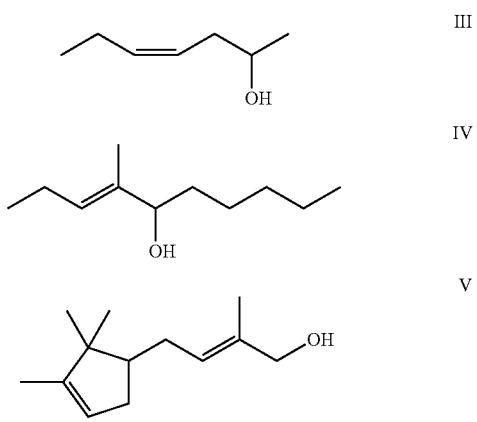

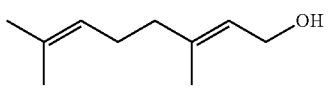

VI

In these cases, Q is a single carbon atom in Formula III and a single covalent bond in Formulae IV, V and VI. However, in the case of Formulae V and VI, each molecule has an additional double bond at a position which corresponds to Q being at least 2. In this case, cyclopropanation of these more remote double bonds also takes place, but this cyclopropanation is only partial. Complete conversion is possible, but only by repeating the process several times.

An example of such a remote cyclopropanation is the complete conversion of nor-Radjanol™ (Formula V) to Javanol™ and Geraniol (Formula VI) to its bis-cyclopropanated Geraniol analog in 3 cyclopropanation cycles and Barbier reaction conditions.

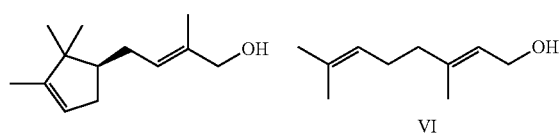

V     VI

BuLi, 0° C. or LiH, 70° C.
then 4 equiv Mg,
4 equiv CH₂Br₂, 70° C.

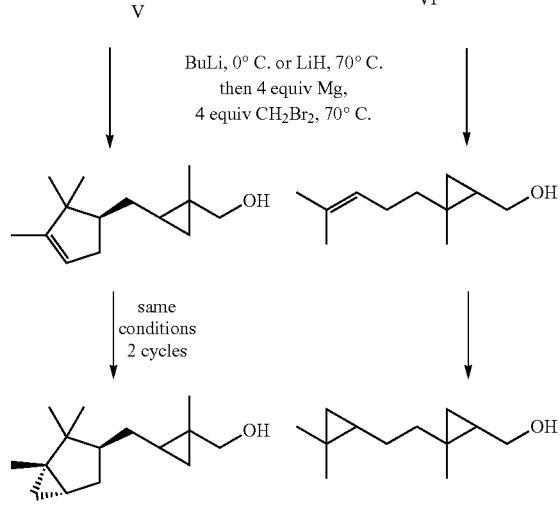

same
conditions
2 cycles

Javanol™

Examples of allylic alcohols (in which Q represents a single bond) that undergo the cyclopropanation reaction using System B include those with the following structures:

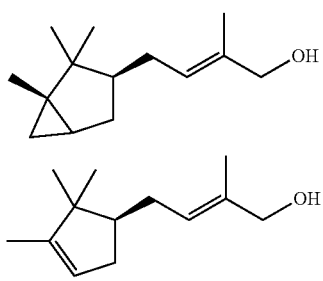

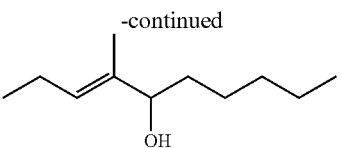

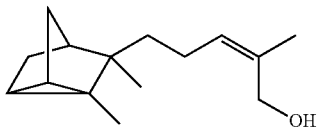 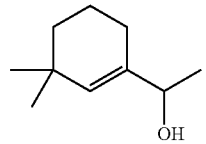

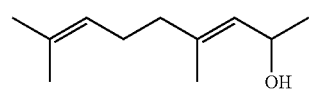 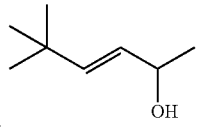

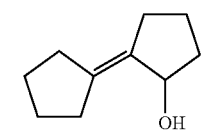 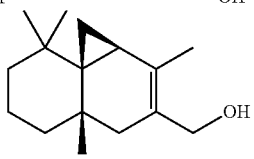

Examples of homoallylic alcohols (in which Q represents a single carbon atom) that undergo reaction with System B include those with the following structures:

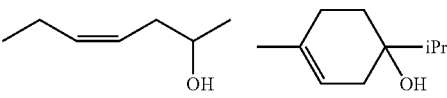

When System B is used, particular examples of processes include:

an allylic alcohol in 2-5 (particularly ≦3) equiv dibromomethane is cyclopropanated by slow addition of 2-5 (particularly ≦3) equiv of a tertiary (α-trisubstituted) Grignard reagent R₃CMgX at 10-20° C. (X=Cl, Br) in ether solvents;

2-5 (particularly ≦3) equiv dibromomethane and 2-5 (particularly ≦3) equiv of a tertiary (α-trisubstituted) Grignard reagent R₃CMgX are added portionwise or continuously but separately to the allylic alcohol in ether solvents.

It is possible to show that these tertiary Grignard reagents give a much more effective cyclopropanation than secondary ones, e.g. isopropyl magnesium chloride (employed by C. Bolm, D. Pupowicz, *Tetrahedron Lett.* 38, 7349-7352, 1997).

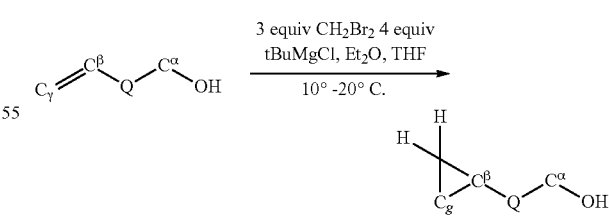

In this case, it is believed (without restricting the invention in any way) that the first equiv of Grignard reagent acts as deprotonation reagent, thus generating an allylic alcoholate of Formula II, and that the other 3 equiv effect cyclopropanation. Other reagents can be used for deprotonation, such as NaH, LiH, organolithium reagents and other Grignard reagents. Yields and selectivities are, under the less drastic conditions of System B, generally higher than those obtained under Barbier conditions. For example, if an allylic alcoholate also comprises a remote alkene (i.e., there are more than 2 carbon atoms between the hydroxy group and the alkene), the allylic alcohol alkene will be cyclopropanated almost exclusively.

In another embodiment of this process, conjugated aldehydes, ketones, acids and esters as well as allylic esters, allylic carbonates and vinyloxiranes of the type shown in the scheme above may be alkylated and cyclopropanated in sequential (tandem) reactions, that is, in situ before work-up. Alkylation of all these substrates gives allylic alcoholates, which are further cyclopropanated according to the methods hereinabove described. This tandem cyclopanation is also possible with allylic alcoholates generated from saturated aldehydes, ketones and esters via addition of alkenyl magnesium halides.

Sequential or tandem reactions, sometimes referred to as "one-pot" reactions, are chemical processes in which two or more consecutive molecular transformations may be carried out without the need to isolate intermediates. The reactions proceed in a consecutive fashion and new bonds and stereo centers are created in a second or subsequent step. Such reactions enhance the synthetic efficiency in the construction of complex molecules from simpler ones. (G. H. Posner, *Chem. Rev.* 86, 831, 1986. L. F. Tietze, U. Beifuss, *Angew. Chem., Int. Ed. Engl.* 32, 131, 1993. T.-L. Ho, *Tandem Organic Reactions*; Wiley: New York, 1992).

Conjugated aldehydes (i.e., aldehydes attached to an ethylenic double bond via a single bond) are first 1,2-alkylated (at the carbonyl group) with an appropriate organomagnesium (RMgX) or organolithium (RLi) reagent followed by (A) addition of magnesium and subsequent cyclopropanation with $CH_2Br_2$ at reflux or (B) cyclopropanation with dibromomethane and tent-butyl magnesium chloride (tBuMgCl) at 10°-20° C.

Examples of conjugated aldehydes that undergo this sequential reaction to the corresponding syn-configured cyclopropane carbinols include those in the following transformations:

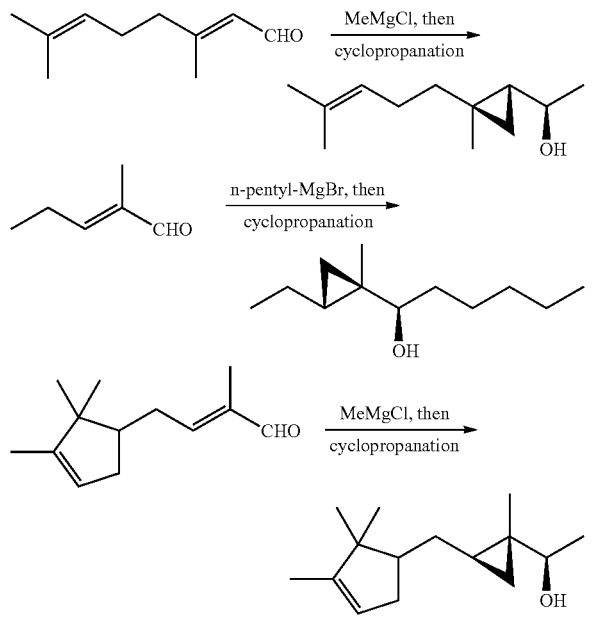

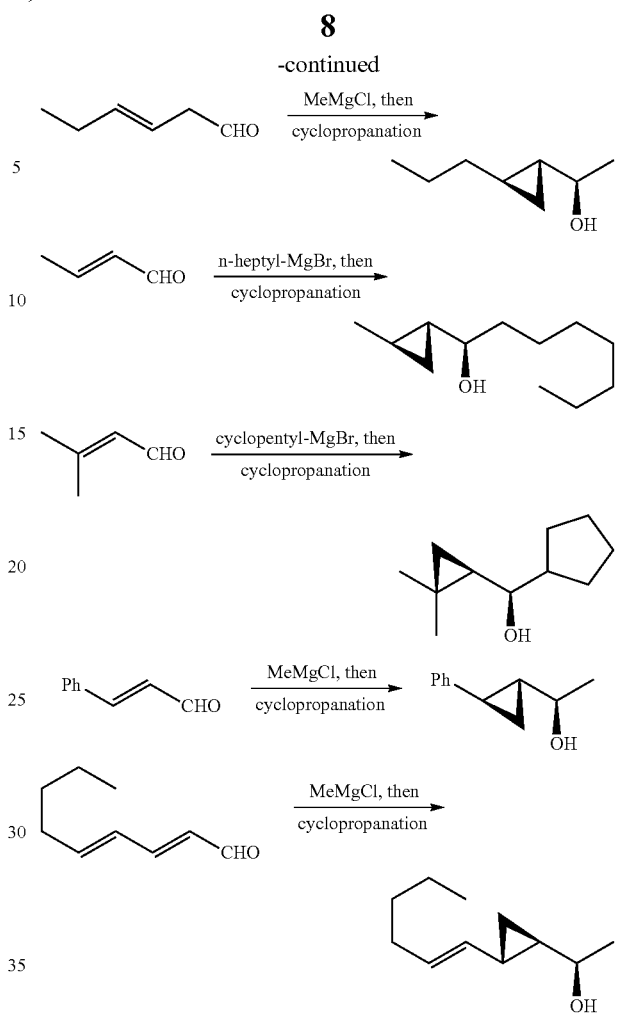

Conjugated ketones are first 1,2-alkylated (at the carbonyl group) with ≧1 equiv of an appropriate organomagnesium (RMgX) or preferably an organolithium (RLi) reagent under cooling followed by cyclopropanation with dibromomethane and tert-Butyl-MgCl at 0°-5° C. A similar tandem reaction, addition of MeLi to a conjugated ketone, followed by a Simmons-Smith cyclopropanation has been reported by T. Cohen et al., *Organic Letters*, 3, 2121, 2001. A subsequent cyclopropanation of the allyloxylithium intermediate with dibromomethane under Grignard conditions, however, is new and more efficient.

Examples of conjugated ketones that undergo this sequential reaction to the corresponding cis-configured cyclopropane carbinols, include those in the following transformations:

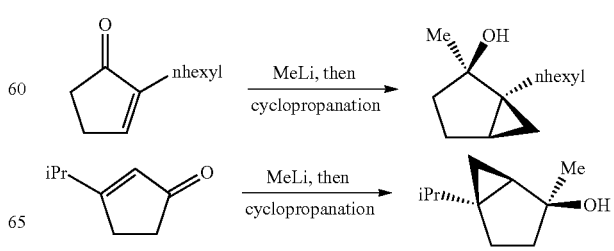

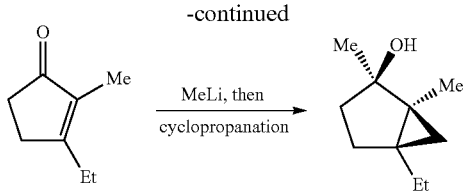

Conjugated esters are first alkylated with ≧2 equiv of an appropriate organomagnesium (RMgX) or preferably an organolithium (RLi) reagent under cooling followed by cyclopropanation with dibromomethane and tert-Butyl-MgCl at 0°-5° C.

Examples of conjugated esters that undergo this sequential reaction include those in the following transformations:

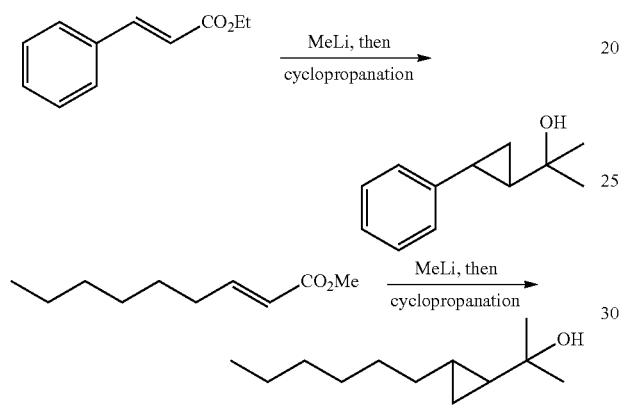

1-Alkenyl halides are first converted to the corresponding 1-alkenyl magnesium reagents by known procedures (as described by K. Nützel in *Methoden der organischen Chemie*, Houben-Weyl, (G. Thieme Verlag, Stuttgart), Vol 13/2a, pp 47-529, 1973) followed by addition of an aldehyde or ketone, followed by (A) Mg/CH$_2$Br$_2$ or (B) CH$_2$Br$_2$/tBuMgCl cyclopropanation of the allyloxy magnesium intermediate. Alternatively, alkenyl halides are converted to the corresponding alkenyllithium reagents by known processes (as described by U. Schöllkopf in *Methoden der organischen Chemie*, Houben-Weyl, Vol 13/2a, pp 47-529, 1973) followed by addition of an aldehyde followed by (A) Mg/CH$_2$Br$_2$ or (B) CH$_2$Br$_2$/tBuMgCl cyclopropanation of the thus-formed allyloxylithium intermediate. Alternatively, alkenyl-lithium reagents can be added to ketones followed by CH$_2$Br$_2$/tBuMgCl cyclopropanation of the thus-formed allyloxylithium intermediate.

Examples of alkenyl halides that undergo this sequential reaction to the corresponding cyclopropane carbinols, include the following transformation:

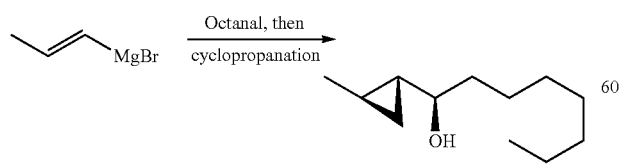

Allylic or homoallylic esters and allylic or homoallylic carbonates are cleaved with an appropriate amount of Grignard reagent (RMgX) or organolithium (RLi) reagent followed by (A) addition of magnesium and subsequent cyclopropanation with CH$_2$Br$_2$ at reflux or (B) addition of dibromomethane and subsequent cyclopropanation with a tertiary Grignard reagent at 10-20° C. Examples of these sequential reactions are given by the following transformations:

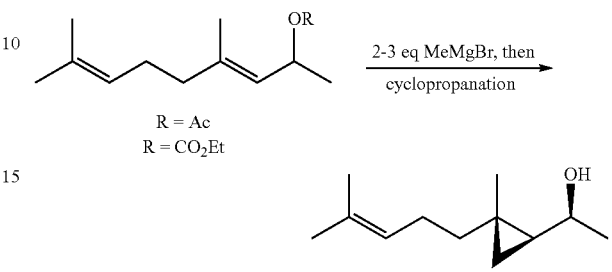

Vinyloxiranes are first alkylated with an appropriate organolithium (RLi) reagent, with or without an additional base to adjust selectivity, followed by (A) addition of magnesium and subsequent cyclopropanation with CH$_2$Br$_2$ at reflux or (B) cyclopropanation with dibromomethane and tert-butyl-MgCl at 10°-20° C. The S$_N$2' selective opening of isoprene oxide with organolithium reagents (RLi) is described in *Tetrahedron Lett.* 22, 577, 1980. Examples of this sequential reaction are given by the following transformations:

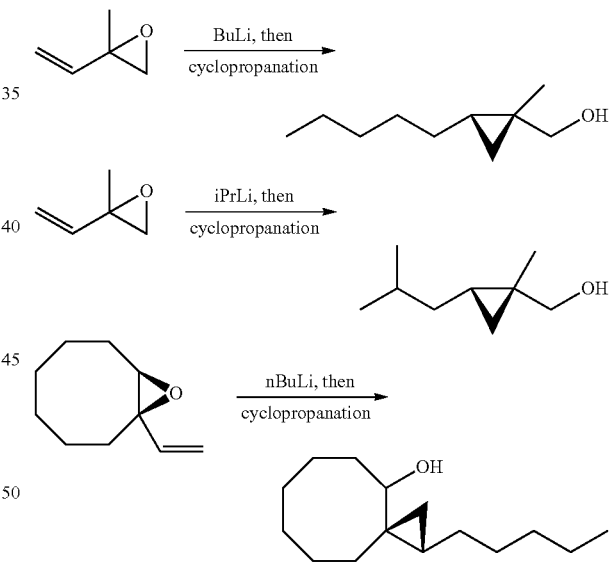

The above embodiments of the cyclopropanation process have many uses, including the relatively easy and inexpensive manufacture of flavour and fragrance ingredients.

Some of the compounds prepared by this method are novel. There is therefore also disclosed the following compounds:

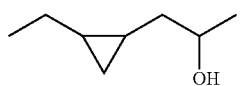

1-(2-ethylcyclopropyl)propan-2-ol

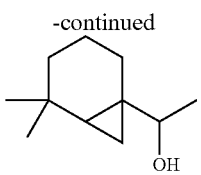

1-(5,5-dimethylbicyclo[4.1.0]heptan-1-yl)ethanol

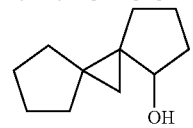

dispiro[4.0.4.1]undecan-4-ol

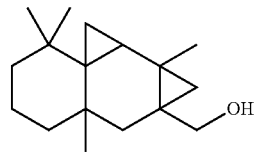

2,2,5a,7a-tetramethyldecahydro-1H-dicyclopropa[b,d]naphthalen-6a-yl)methanol

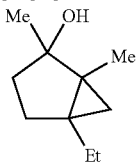

5-ethyl-1,2-dimethylbicyclo[3.1.0]hexan-2-ol

The invention is now further described with reference to the following non-limiting examples.

EXAMPLE 1

(1-methyl-2-(((1S,3R,5R)-1,2,2-trimethylbicyclo[3.1.0]hexan-3-yl)methyl)-cyclopropyl)methanol (Javanol™)

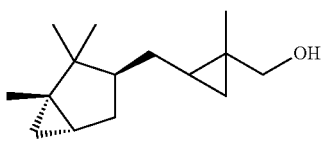 [SMILES: CC1(CO)CC1C[C@H]1C[C@@H]2C[C@]2(C)C1(C)C]

System A: (E)-2-methyl-4-(2,2,3-trimethylcyclopent-3-enyl)but-2-en-1-ol (J. A. Bajgrowicz, I. Frank, G. Frater, M. Hennig, *Helv. Chim. Acta.* 81, 1349-1358, 1998) (200 g, 1 mol) and lithium hydride (10 g, 1.24 mol) in tetrahydrofuran are heated under strong stirring and argon for 6 h at 65° C. until hydrogen evolution ceases. Magnesium turnings (100 g, 4.1 mol) and 1900 ml tetrahydrofuran are added at 25° C. After addition of dibromoethane (8.5 g, 50 mmol) the mixture is heated to 65° C., where dibromomethane (280 ml, 4 mol) is added over 7 h. After another hour at 65° C. the suspension is quenched with 2M HCl under cooling. Tert-Butyl methyl ether extraction, washing of the organic phase with H$_2$O until pH 7, drying over MgSO$_4$ and concentration gives a crude (65% corr.) mono- and biscyclopropane mixture (75:20), which is, after another two reaction cycles, giving 95 g (43%) of pure Javanol after distillation (100° C./0.05 Torr), whose analytical data (NMR, MS, IR, odor) are consistent with the ones described for this compound in the literature (J. A. Bajgrowicz, G. Frater, EP 801049, priority 9.4.1997 to Givaudan-Roure).

System B: (E)-2-methyl-4-((1S,3S,5R)-1,2,2-trimethylbicyclo-[3.1.0]hexan-3-yl)but-2-en-1-ol (5 g, 24 mmol) (F. Schröder, WO 2006066436, priority 20.12.2005 to Givaudan) is added undercooling and stirring to methyl magnesium chloride 3M in tetrahydrofuran (8 ml, 24 mmol) under nitrogen. Dibromomethane and tert-butyl magnesium chloride are added at a temperature of 10°-20° C. The dibromomethane and tert-butyl magnesium chloride are each added in 3 portions, one portion of dibromomethane (4.2 g, 24 mmol) followed by a portion of tert-butyl-magnesium chloride (12 ml, 24 mmol). After the addition of each pair of portions (72 mmol) the mixture is stirred for an appropriate time at room temperature. When complete or nearly complete conversion is reached, as checked by GC, the mixture is quenched by addition of conc. NH$_4$Cl. Tert-Butyl methyl ether extraction, washing of the organic phase with H$_2$O until pH 7, drying over MgSO$_4$ and concentration gives 16.6 g of an an oily residue, which is bulb-to bulb-distilled at 120° C./0.07 Ton giving 4.7 g (89%) of Javanol (dr=1:1), whose analytical data are consistent with the ones described for this compound in the literature (J. A. Bajgrowicz, G. Frater, EP 801049, priority 9.4.1997 to Givaudan-Roure).

EXAMPLE 2

(trans)-(1-methyl-2-(((R)-2,2,3-trimethylcyclopent-3-enyl)methyl)cyclopropyl)-methanol

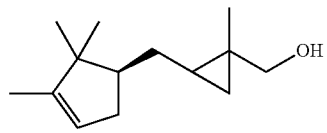

Prepared as described in Example 1 (System B) from nor-Radjanol (12.6 g, 65 mmol) (J. A. Bajgrowicz, I. Frank, G. Frater, M. Hennig, *Helv. Chim. Acta* 81, 1349-1358, 1998), methyl magnesium chloride 3M in tetrahydrofuran (22 ml, 65 mmol), dibromomethane (3×10 g, 0.17 mol) and tert-butyl magnesium chloride 2M in diethyl ether (3×28 ml, 0.17 mol). Work-up and bulb-to bulb-distillation at 110° C./0.1 Torr gives 12.5 g (93%) of a colorless oil (dr=1:1), whose analytical data (NMR, MS, IR, odor) are consistent with the ones described for this compound in the literature (J. A. Bajgrowicz, I. Frank, G. Frater, M. Hennig, *Helv. Chim. Acta* 81, 1349-1358, 1998).

EXAMPLE 3

(syn,trans)-1-(2-ethyl-1-methylcyclopropyl)hexan-1-ol

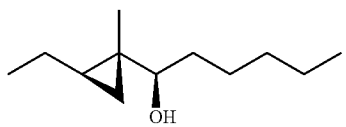

This compound was prepared using both Systems A and B of Example 1

System A: n-Butyl lithium (11 ml, 17 mmol) is added dropwise and under cooling to (E)-4-methyldec-3-en-5-ol (R. Kaiser, D. Lamparsky, EP 45453, Givaudan, 1980) (3 g, 17 mmol). Magnesium powder (2.6 g, 0.1 mol) is added and the Barbier reaction started with a few drops of dibromomethane (18 g, 0.1 mol), which is then added at 60° C. over 1 h. After 18 h at 60° C. the mixture is worked-up as above. Bulb-to-bulb distillation at 55° C./0.05 mbar gives 2.15 g (68% corr.) of a colorless oil (syn/anti=97:3).

System B: (E)-4-methyldec-3-en-5-ol (R. Kaiser, D. Lamparsky, EP 45453, Givaudan 1980) (25 g, 0.15 mol) is added under cooling and stirring to methyl magnesium chloride 3M in tetrahydrofuran (49 ml, 0.15 mol) under nitrogen. Alternatively, the (E)-dec-3-en-5-olate magnesium halide is prepared from (E)-2-methylpent-2-enal (12.6 g, 0.15 mol) and pentane-magnesium bromide 2 M in diethyl ether (75 ml, 0.15 mol). Dibromomethane (77 g, 0.44 mol) is added to the the Grignard product followed by dropwise addition of tert-butyl magnesium chloride 2M in diethyl ether (220 ml, 0.44 mol) at 10°-20° C. After 16 h at 25° C. 2M HCl is added. Tert-Butyl methyl ether extraction, washing of the organic phase with conc. $NaHCO_3$, $H_2O$ and conc. NaCl, drying over $MgSO_4$, filtration and concentration gives 30.3 g of an oily residue, which is distilled at 45° C./0.03 Torr giving 24.4 g (90%) product as colorless oil.

Odour: green, fresh, spicy, chocolate. $^1H$ NMR ($CDCl_3$): δ-0.05 (m, 1H), 0.5 (2H), 0.9 (t, 3 H), 0.99 (t, 3H), 1.01 (s, 3H), 1.25-1.35 and 1.35-1.6 (11H), 2.7 (dd, 1H) ppm. $^{13}C$-NMR ($CDCl_3$): δ 11.6 (q), 14.0 (q), 14.3 (q), 17.8 (t), 22.0 (t), 22.6 (t), 24.0 (d), 24.9 (s), 26.0 (t), 32.0 (t), 33.9 (t), 80.9 (d). syn-configuration confirmed by NMR-analysis of the ethyl ether. MS (EI): m/z (%) 166 ($[M-18]^+$, 3), 141 (5), 128 (15), 113 (10), 99 (32), 84 (35), 72 (85), 71 (100), 69 (60), 55 (70), 43 (75).

EXAMPLE 4

(cis,syn)-1-(-2-ethylcyclopropyl)propan-2-ol

System A: Prepared as described in Example 3 from (Z)-hept-4-en-2-ol (S. C. Watson, D. B. Malpass, G. S. Yeargin, DE 2430287, Texas Alkyls Inc. USA, 1975) (3 g, 26 mmol), n-butyl lithium (16.5 ml, 26 mmol), magnesium powder (3.8 g, 0.16 mol) and dibromomethane (27 g, 0.16 mol). After 18 h at 60° C. work-up and bulb-to-bulb distillation at 55° C./0.05 mbar gives 2.1 g (57% corr) of a colorless oil (syn/anti=73:27).

System B: Prepared as described in Example 7 but in 2 reaction cycles from (Z)-hept-4-en-2-ol (4 g, 35 mmol) and dibromomethane (2×18.2 g, 0.2 mol) in diethyl ether by dropwise addition of tert-butyl magnesium chloride 2M in diethyl ether (2×52 ml, 0.2 mol) at 10°-20° C. Work-up after 18 h at 25° C. gave 5.7 g of a crude oil which was distilled at 45° C./12 mbar, giving 2.5 g (55%) of a colorless oil (97% purity, syn/anti=83:17).

$^1$H-NMR ($CDCl_3$): δ-0.2 (m, 1H), 0.6-0.8 (2 m, 2H), 1.0 (t, 3H), 1.2 (d, 3H), 1.2-1.4 (3H), 1.6 (1H), 2.3 (br, OH), 3.9 (m, 1H) ppm. $^{13}C$-NMR (syn-isomer): δ 10.5 (t), 12.4 (d), 14.2 (q), 16.6 (d), 22.0 (t), 23.0 (q), 37.8 (t), 68.8 (d). $^{13}C$-NMR (anti-isomer): δ 10.5 (t), 12.3 (d), 14.2 (q), 17.3 (d), 22.1 (t), 23.1 (q), 37.9 (t), 68.6 (d). Syn-configuration confirmed by conversion to the camphanoyl ester and X-ray analysis. MS (EI): m/z (%)110 ($[M-18]^+$, 3), 95 (12), 84 (11), 81 (20), 68 (23), 55 (50), 45 (100). Retention times: 5.82 (syn), 5.86 (anti). IR (film): 3340 (br), 2961 (s), 2929 (m), 2872 (m), 1456 (m), 1374 (m), 1308 (w), 1120 (m), 1084 (m), 1063 (m), 1022 (m), 994 (w), 940 (m), 927 (m), 855 (w), 815 (w), 739 (w).

EXAMPLE 5

(trans)-(2-methyl-2-(4-methylpent-3-enyl)cyclopropyl)methanol

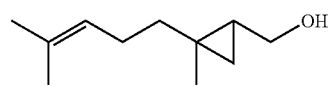

Prepared according to Example 1 (System A) from (E)-Geraniol (50 g, 0.32 mol), lithium hydride (3.4 g, 0.4 mol) in tetrahydrofuran (350 ml), magnesium powder (31.5 g, 1.3 mol) and dibromomethane (225 g, 1.3 mol). Work-up after 4 h at 65° C. and bulb-to-bulb distillation gave 36 g (66%) of a colorless oil, whose analytical data are consistent with the ones described for this compound in the literature (G. A. Molander, L. S. Harring, *J. Org. Chem.* 54, 3525-3532, 1989).

EXAMPLE 6

(trans)-(2-(2-(2,2-dimethylcyclopropyl)ethyl)-2-methylcyclopropyl)methanol

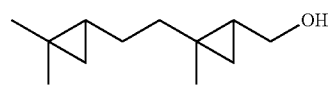

The (2-methyl-2-(4-methylpent-3-enyl)cyclopropyl) methanol obtained in Example 5 was subjected to another 2 reaction cycles under the conditions of Example 1 (System A) using the same amount of reagents as in Example 24 giving after work-up and distillation 15 g (25% from Geraniol) of a colorless oil, whose analytical data are consistent with the ones described for this compound in the literature (H. Sakauchi, H. Asao, T. Hasaba, S. Kuwahara, H. Kiyota, *Chemistry & Biodiversity*, 3, 544-552, 2006).

EXAMPLE 7

(cis)-{2-[2-(2,3-Dimethyl-tricyclo[2.2.1.0(2,6)]hept-3-yl)-ethyl]-1-methyl-cyclopropyl}-methanol

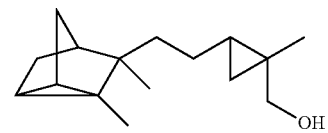 [SMILES: CC1(CO)CC1CCC1(C)C2CC3C(C2)C31C]

Prepared as described in Example 1 (System B) from (E)-2-methyl-4-((1S,3S,5R)-1,2,2-trimethylbicyclo[3.1.0]-hexan-3-yl)but-2-en-1-ol (M. Tamura, G. Suzukamo, *Tetra-* hedron Lett. 22, 577, 1981) (5.3 g, 24 mmol), methyl magnesium chloride 3M in tetrahydrofuran (8 ml, 24 mmol), dibromomethane (2×6.3 g, 72 mmol) and tert-butyl magnesium chloride 2M in diethyl ether (2×18 ml, 72 mmol). Work-up after 18 h and bulb-to-bulb distillation gives 3.85 g of a colorless oil (68%). Odour: woody, creamy, weak. $^1$H NMR (CDCl$_3$): δ 0.08 (dd, 1H), 0.45 (dd, 1H), 0.6 (m, 1H), 0.8 and 0.82 (2s, 3H), 0.83 and 0.86 (2s, 3H), 1.0 (s, 3H), 1.05 (2H), 1.1-1.45 (7H), 1.5-1.6 (3H), 3.5-3.6 (2d, 2H) ppm. $^{13}$C-NMR (CDCl$_3$): δ 10.7 (2 q), 17.5 (2 t), 17.6 (2 q), 19.4 (2 d), 19.5 (2 d), 22.3 (s), 22.7 (2 q), 24.3 (2 t), 25.9 (2 d), 27.5 (2 s), 30.9 (2 t), 31.4 (2 t), 34.8 (2 t), 38.1 and 38.2 (2 d), 45.6 (2 q), 67.3 and 67.4 (2 t). MS (EI): m/z (%) 234 (M$^+$, 3), 219 ([M-15]$^+$, 1), 203 ([M-18]$^+$, 2), 161 (7), 121 (82), 107 (20), 93 (100), 91 (40), 79 (32), 77 (25), 55 (25), 41 (40).

EXAMPLE 8

(RS)-1-((1RS,6SR)-5,5-dimethylbicyclo[4.1.0]heptan-1-yl)ethanol

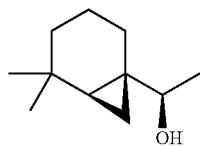

Prepared as described in Example 1 (System B) from 1-(3,3-dimethylcyclohex-1-enyl)ethanol (A. T. Levorse, U.S. Pat. No. 5,234,902, priority 28.2.1992 to IFF) (3.7 g, 24 mmol), methyl magnesium chloride 3M in tetrahydrofuran (8 ml, 24 mmol), dibromomethane (2×6.3 g, 72 mmol) and tert-butyl magnesium chloride 2M in diethyl ether (2×18 ml, 72 mmol). Work-up after 20 h at 25° C. and bulb-to-bulb distillation gives 3.2 g (82%) product (syn/anti=97:3). Odour: Agrestic, strong. $^1$H NMR (CDCl$_3$): δ 0.18 (m, 1H), 0.44 (m, 2H), 0.85-1.5 (6H), 0.95 (s, 3H), 1.05 (s, 3H), 1.19 (d, 3H), 1.95 (1H), 3.02 (m, 1H). $^{13}$C-NMR: (CDCl$_3$): δ 15.8 (t), 18.9 (t), 19.4 (q), 23.2 (t), 26.1 (s), 27.8 (s), 28.4 (d), 30.9 (q), 30.5 (q), 35.2 (t), 76.4 (d). Relative configuration confirmed by NMR-analysis of the benzyl ether and X-ray analysis of the Camphanate. MS (EI): m/z (%) 168 (M$^+$, 1), 150 ([M-18]$^+$, 20), 135 (30), 121 (25), 109 (50), 107 (65), 93 (50), 82 (50), 81 (55), 79 (56), 69 (65), 59 (65), 55 (55), 43 (100).

EXAMPLE 9

(syn,trans)-1-((E)-2-methyl-2-(4-methylpent-3-enyl)cyclopropyl)ethanol

This example shows the preparation of the abovementioned compound, using one of four initial stages (a)-(d) below:

a) (E)-4,8-dimethylnona-3,7-dien-2-ol (EP 0743297 to Givaudan) (3.6 g, 24 mmol) and methyl magnesium chloride 3M in tetrahydrofuran (8 ml, 24 mmol).

b) (E)-Citral (4 g, 24 mmol) and methyl magnesium chloride 3M in tetrahydrofuran (8 ml, 24 mmol).

c) 4,8-dimethylnona-3,7-dien-2-yl acetate (V. K. Agarwal, T. K. Thappa, S. Agarwal, M. S. Mehra, K. L. Dhar, C. K. Atal, *Indian Perfumer* 27, 112-118, 1983) (5 g, 24 mmol) and methyl magnesium chloride 3M in tetrahydrofuran (19 ml, 60 mmol).

d) 4,8-dimethylnona-3,7-dien-2-yl ethyl carbonate (J.-P. Barras, B. Bourdin, F. Schröder, *Chimia* 60, 574-579, 2006) (6 g, 24 mmol) and methyl magnesium chloride 3M in tetrahydrofuran (25 ml, 60 mmol).

In each case, subsequent cyclopropanation is carried out (according to Example 1, Method B) with dibromomethane (3×4.2 g, 72 mmol) and tert-butyl magnesium chloride 2M in diethyl ether (3×12 ml, 72 mmol). Work-up after 16 h at 25° C. and bulb-to-bulb distillation gives 3.7 g (86%) product. Odour: citrus, weak. Analytical data identical with the ones reported for this compound (G. A. Molander, L. S. Harring, *J. Org. Chem.* 54, 3525-3532, 1989). Syn-configuration confirmed by COSY, HSQC, NOESY in CDCl$_3$.

EXAMPLE 10

(syn,trans)-1-(2-tert-butylcyclopropyl)ethanol

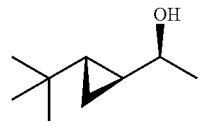

Tert-butyl magnesium chloride 2M in diethyl ether (13 ml, 26 mmol) is added dropwise and at 10°-20° C. to (E)-5,5-dimethylhex-3-en-2-ol (P. Jacob III, H. C. Brown, *J. Org. Chem.* 42, 579, 1977) (0.7 g, 5.3 mmol) in dibromomethane (4.6 g, 26 mmol). After 24 h at 25° C. 2M HCl is added. Tert-Butyl methyl ether extraction, washing of the organic phase with conc. NaHCO$_3$ and conc. NaCl, drying over MgSO$_4$, filtration and concentration gives 1.8 g of an oily residue, which is purified by flash chromatography over silicagel (hexane/tert-Butyl methyl ether gradient 95:5 to 80:20) giving 0.6 g (80%) of a colorless liquid. $^1$H NMR (CDCl$_3$): δ 0.3 (m, 1H), 0.45 (ddd, 1H), 0.53 (ddd, 1H), 0.85 (s, 9H), 1.27 (d, 3H), 1.65 (br, OH), 3.07 (dq, 1H) ppm. $^{13}$C-NMR: δ 6.4 (t), 22.7 (q), 23.0 (d), 28.4 (3C, q), 28.6 (d), 29.1 (s), 73.1 (d). syn-configuration confirmed by HMBC, HMQC, COSY, NOESY in DMSO. MS (EI): m/z (%) 124 ([M-18]$^+$, 4), 109 (11), 87 (7), 85 (5), 83 (6), 70 (100), 57 (16), 55 (53), 43 (24), 41 (25).

EXAMPLE 11

(syn)-dispiro[4.0.4.1]undecan-4-ol

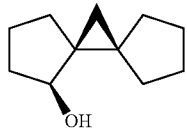

Prepared as described in Example 8 from 2-cyclopentylidene-cyclopentanol (A. Martin, EP 770671, priority 30.10.1996 to Quest International B.V.) (5 g, 32 mmol), dibromomethane (23 g, 0.13 mol) in tetrahydrofuran (20 ml) using tert-butyl magnesium chloride 2M in diethyl ether (66 ml, 0.13 mol) at 10°-20° C. Work-up after 16 h at 25° C. and flash chromatography over Silicagel (hexane/tert-butyl methyl ether 3:1) gives 3.4 g (64%) product as a colorless oil. Odour: animalic, agrestic, strong. $^1$H NMR (CDCl$_3$): δ 0.34 (d, 1H), 0.71 (d, 1H), 1.4-1.9 (14H), 3.8 (dd, 1H) ppm. $^{13}$C-NMR: δ 22.4 (t), 22.5 (t), 25.8 (t), 26.2 (t), 30.7 (t), 32.3 (s), 32.4 (t), 32.7 (t), 35.8 (s), 36.1 (t), 75.5 (d). Syn-configuration confirmed by COSY, HRQC, HMBC, NOESY. MS (EI): m/z (%) 166 [M]$^+$, 1), 148 ([M-18]$^+$, 1), 137 (3), 133 (5), 119 (14), 105 (10), 97 (50), 91 (25), 85 (60), 84 (35), 83 (36), 82 (55), 79 (38), 67 (100), 55 (32), 41 (35). IR (film): 3344 (br, OH), 2947 (s), 2863 (s), 1447 (m), 1327 (w), 1300 (w), 1168 (w), 1140 (w), 1074 (m), 1028 (m), 1008 (m), 964 (m), 893 (w), 851 (w), 656 (br,w).

EXAMPLE 12

((11S,5aS,6aR,7aR,7bS)-2,2,5a,7a tetramethyl-decahydro-1H-dicyclopropa[b,d]naphthalen-6μ-yl)methanol

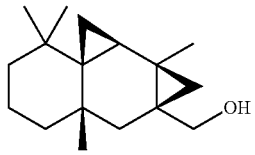 [SMILES: CC1(C)CCC[C@@]2(C)C[C@]3(CO)C[C@]3(C)[C@@H]3C[C@]312]

Prepared as described in Example 1 (System B) from ((11S,5aS,8aS)-2,2,5a,8-tetramethyl-1,2,3,4,5,5a,6,8a-octahydrocyclopropa[d]naphthalen-7-yl)methanol (P. C. Traas, H. Boelens, *Recueil des Travaux Chimiques des Pays-Bas* 92, 985-995, 1973), (1 g, 4.4 mmol), dibromomethane (5×0.75 g, 21 mmol) and tert-butyl magnesium chloride 2M in diethyl ether (5×2.1 ml, 21 mmol). Work-up after 18 h and flash chromatography (hexane/tert-butyl methyl ether 9:1→1:1) over Silicagel gives 0.75 g (70%) white crystals. M.p. 93° C. from hexane. $^1$H NMR (CDCl$_3$): δ-0.01 (dd, 1H), 0.15 (2 m, 2H), 0.3 (d, 1H), 0.6 (s, 3H), 1.0 (s, 3H), 1.04 (s, 3H), 1.1-1.2 (m, 2H), 1.2-1.3 (m, 2H), 1.33 (s, 3H), 1.4-1.6 (4H), 1.7-1.85 (m, 1H), 3.33 (d, 1H), 3.6 (d, 1H) ppm. $^{13}$C-NMR (CDCl$_3$): δ 7.15 (t), 19.5 (t), 19.7 (s), 21.7 (s), 22.7 (q), 23.7 (t), 24.8 (d), 26.9 (q), 28.0 (q), 29.2 (q), 31.8 (s), 33.6 (s), 34.4 (s), 37.1 (t), 40.9 (t), 42.9 (t), 69.7 (t). Relative configuration confirmed by COSY, HSQC, HMBC, NOESY in C$_6$D$_6$. MS (EI): m/z (%) 248 [M]$^+$, 6), 233 ([M-15]$^+$, 4), 217 (17), 178 (17), 177 (100), 161 (15), 159 (20), 147 (19), 145 (27), 123 (48), 121 (65), 119 (49), 109 (66), 107 (65), 105 (68), 95 (69), 93 (74), 91 (66), 69 (48), 67 (28), 55 (54), 41 (58). IR (film): 3310 (br, OH), 2900 (m), 1483 (w), 1454 (w), 1438 (w), 1371 (w), 1320 (w), 1104 (w), 1061 (w), 1015 (s), 969 (w), 907 (w), 728 (w).

EXAMPLE 13

(cis)-3-isopropyl-6-methylbicyclo[4.1.0]heptan-3-ol

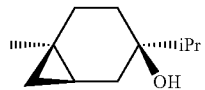

Prepared as described in Example 10 from Terpinen-4-ol (2 g, 13 mmol) and dibromomethane (9.15 g, 52 mmol) in diethyl ether by dropwise addition of tent-butyl magnesium chloride 2M in diethyl ether (26 ml, 52 mmol) at 10°-20° C. Work-up after 16 h at 25° C. and bulb-to-bulb distillation gave 2.1 g (85%) of a colorless oil. Odour: Agrestic. $^1$H-NMR (CDCl$_3$): δ 0.3 (dd, 1H), 0.43 (dd, 1H), 0.6 (dddd, 1H), 0.89 (d, 3H), 0.91 (d, 3H), 1.03 (s, 3H), 1.1-1.2 (m, 2H), 1.2-1.3 (m, 1H), 1.5-1.7 (2 m, 2H), 1.75-1.9 (2H), 2.2 (m, 2H) ppm. $^{13}$C-NMR: δ 14.4 (s), 16.2 (q), 16.4 (q), 17.7 (d), 19.9 (t), 27.2 (q), 28.1 (t), 31.6 (t), 31.9 (d), 35.7 (t), 72.8 (s). syn-configuration confirmed by COSY, HSQC, HMBC, NOESY in CDCl$_3$. MS (EI): m/z (%) 168 [M]$^+$, 3), 150 ([M-18]$^+$, 8), 125 (32), 107 (65), 86 (38), 71 (80), 43 (100). IR (film): 3419 (br), 2936 (m), 2863 (m), 1458 (m), 1379 (w), 1302 (w), 1225 (w), 1133 (m), 1049 (w), 992 (s), 957 (w), 906 (w), 863 (w).

EXAMPLE 14

(trans,syn)-1-((1-methyl-2-((2,2,3-trimethylcyclopent-3-enyl)methyl)-cyclopropyl)ethanol

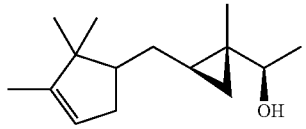 [SMILES: CC1=CCC(C[C@@H]2C[C@@]2(C)[C@@H](C)O)C1(C)C]

Prepared as described in Example 1 (System B) from nor-Radjaldehyde (U.S. Pat. No. 4,052,341 to Givaudan Corp.) (4.6 g, 24 mmol), methyl magnesium chloride 3M in tetrahydrofuran (8 ml, 24 mmol), dibromomethane (2×6.3 g, 72 mmol) and tert-butyl magnesium chloride 2M in diethyl ether (2×18 ml, 72 mmol). Work-up after 5 h at 25° C. and distillation gives 3.5 g (65%) of a colorless oil (syn, dr=1:1). Odour: sandalwood, green. $^1$H NMR (CDCl$_3$): δ 0.07 and 0.05 (1H), 0.55 (m, 2H), 0.75 (2 s, 3H), 1.0 (s, 3H), 1.05 (s, 3H), 1.2 (2 d, 3H), 1.2-1.5 (3H), 1.6 (s, 3H), 1.7-2.0 (2H), 2.35 (1H), 3.0 (1H), 5.25 (1H) ppm. $^{13}$C-NMR: δ 11.3 and 12.1 (q), 12.6 (q), 18.2 and 18.7 (t), 19.2 (q), 19.5 and 19.6 (q), 20.4 and 21.0 (d), 25.7 and 25.8 (q), 28.5 and 29.0 (t), 35.6 and 35.7 (t), 47.0 (d), 76.4 (d), 121.7 and 121.8 (d), 149.0 (s). syn-configuration confirmed by NMR-analysis of the ethyl ether. MS (EI): m/z (%) 222 ([M]$^+$, 1), 204 ([M-18]$^+$, 5), 189 (8) 153 (24), 135 (21), 134 (22), 133 (15), 121 (60), 109 (64), 108 (80), 107 (70), 95 (60), 94 (35), 93 (100), 91 (44), 81 (29), 79 (58), 77 (34).

EXAMPLE 15

(syn)-1-(2-propylcyclopropyl)ethanol

Prepared as described in Example 1 (System B) from E-hex-2-enal (2.35 g, 24 mmol), methyl magnesium chloride 3M in tetrahydrofuran (8 ml, 24 mmol), dibromomethane (3×5.5 g, 96 mmol) and tert-butyl magnesium chloride 2M in diethyl ether (3×16 ml, 96 mmol). Work-up after 18 h at 25° C. and bulb-to-bulb distillation gives 2.8 g (90%) of a colorless oil (syn/anti=87:13). $^1$H NMR (CDCl$_3$): δ 0.3 (m, 1H), 0.45 (m, 1H), 0.6 (m, 1H), 0.65 (1H), 0.9 (t, 3H), 1.15 (m, 2H), 1.25 (d, 3H), 1.38 (m, 2H), 1.7 (br, OH), 3.1 (m, 1H) ppm. $^{13}$C-NMR (syn-isomer): δ 10.3 (t), 13.9 (q), 16.4 (d), 22.55 (q), 22.6 (t), 27.0 (d), 35.8 (t), 72.5 (d). $^{13}$C-NMR (anti-isomer): δ 9.4 (t), 13.9 (q), 17.0 (d), 22.2 (q), 22.8 (t), 26.8 (d), 35.85 (t), 72.3 (d). Syn-configuration confirmed by COSY, HSQC, NOESY. MS (EI): m/z (%) 110 ([M-18]$^+$, 4), 95 (18) 81 (25), 71 (55), 58 (100), 57 (70), 56 (62), 55 (92), 45 (69), 43 (90).

EXAMPLE 16

(syn)-1-(2-methyl-cyclopropyl)-octan-1-ol

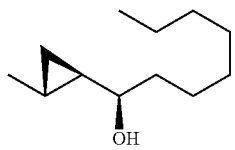

Prepared as described in Example 3 (System B) from heptyl magnesium bromide (prepared from heptyl bromide (26 g, 0.14 mol) and magnesium (3.43 g, 0.14 mol) in tetrahydrofuran (68 ml) at 70° C.), E-crotonaldehyde (8.4 g, 0.12 mol), dibromomethane (62.5 g, 0.36 mol) and of tert-butyl magnesium chloride 2M in diethyl ether (3×60 ml, 0.36 mol) at 10°-20° C. Work-up and distillation at 60° C./0.04 Torr gave 24.4 g (86%) of the trans-isomer as colorless oil.

This compound was also prepared by Grignard reaction of Octanal (18 g, 0.14 mol) with E/Z-1-propenyl magnesium bromide (prepared from magnesium (3.8 g, 0.14 mol), 1-bromo-propene (17 g, 0.14 mol) in tetrahydrofuran (60 ml) at 60° C.) followed by tandem cyclopropanation and work-up as described in the first part of example 14 giving 23.5 g (83%) product (cis/trans=1:1)

Odour: green, earthy, substantive. $^1$H NMR (CDCl$_3$) (trans-isomer): δ 0.25 (m, 1H), 0.4 (m, 1H), 0.6 (m, 1H), 0.9 (t, 3H), 1.05 (d, 3H), 1.2-1.45 (10H), 1.5-1.55 (3H), 2.88 (m, 1H) ppm. $^{13}$C-NMR (CDCl$_3$) (trans-isomer): δ 10.7 (t), 11.15 (d), 14.1 (q), 18.3 (q), 22.6 (t), 25.7 (t), 26.9 (d), 29.3 (t), 29.7 (t), 31.8 (t), 37.4 (t), 76.4 (d). syn-configuration confirmed by NMR-analysis of the ethyl ether. MS (EI): m/z (%) 166 ([M-18]$^+$, 2), 85 (100), 67 (32), 57 (50), 55 (30), 43 (42), 41 (45).

EXAMPLE 17

(syn,trans)-cyclopentyl(2-isopropylcyclopropyl)methanol

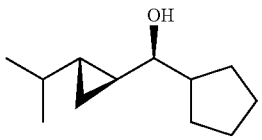

Prepared as described in Example 3 (System B) from cyclopentyl magnesium bromide 2M in diethyl ether (5 ml, 10 mmol), E-4-methyl-2-pentenal (1 g, 10 mmol), dibromomethane (5.2 g, 30 mmol) and tert-butyl magnesium chloride 2M in diethyl ether (15 ml, 30 mmol) at 0°-10° C. Work-up and bulb-to-bulb distillation at 0.05 mbar gave 1 g (50%) of a colorless oil (syn/anti=99:1). $^1$H NMR (CDCl$_3$): δ 0.3 (m, 1H), 0.4 (m, 1H), 0.5 (m, 1H), 0.75 (m), 1.0 (2d, 6H), 1.2-1.7 (8H), 1.7-1.85 (2H), 2.05 (m, 1H), 2.75 (m, 1H) ppm. $^{13}$C-NMR (CDCl$_3$): δ 9.6 (t), 21.9 (q), 22.2 (q), 24.2 (d), 25.55 (t), 25.6 (t), 25.8 (t), 28.2 (t), 29.1 (t), 32.5 (d), 46.3 (d), 79.7 (d). Syn-configuration assigned by COSY, HMBC, HSQC, NOESY in CDCl$_3$. MS (EI): m/z (%) 164 ([M-H$_2$O]$^+$, 1), 121 (3), 113 (13), 95 (36), 81 (8), 71 (7), 69 (8), 67 (8), 57 (100), 55 (12).

EXAMPLE 18

(syn,trans)-1-(2-phenyl-cyclopropyl)-ethanol

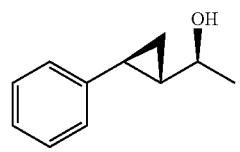

Prepared as described in Example 1 (System B) from E-cinnamon aldehyde (3.2 g, 24 mmol), methyl magnesium chloride 3M in tetrahydrofuran (8 ml, 24 mmol), dibromomethane (2×6.3 g, 72 mmol) and tert-butyl magnesium chloride 2M in diethyl ether (2×18 ml, 72 mmol). Work-up after 18 h at 25° C. and bulb-to-bulb distillation gives 3.3 g (83%) of a colorless oil (syn/anti=82:18), whose analytical data are identical to the ones described for this compound in the literature (Charette, A. B.; Lebel, H. *J. Org. Chem.* 60, 2966-2967, 1995).

EXAMPLE 19

(RS)-1-((1RS,2SR)-2-((E)-hex-1-enyl)cyclopropyl)ethanol

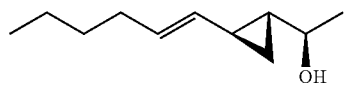

Prepared as described in Example 1 (System B) from methyl magnesium chloride 3M in tetrahydrofuran (7.3 ml, 21 mmol), (2E,4E)-nona-2,4-dienal (3 g, 21 mmol), dibromomethane (15 g, 87 mmol) and tert-butyl magnesium chloride 2M in diethyl ether (43 ml, 87 mmol) at 0°-10° C. Work-up after 18 h and bulb-to-bulb distillation at 80° C./0.05 mbar gave 3.1 g (77%) of a colorless oil (syn/anti=83:17). Odour: fruity, pear, green. $^1$H NMR (CDCl$_3$): δ $^1$H NMR (CDCl$_3$): δ 0.5 (m, 1H), 0.7 (m, 1H), 0.8-1 (2H), 0.9 (t, 3H), 1.2-1.4 (6H), 1.8-2.0 (3H), 3.2 (m, 1H), 5.0 (m, 1H), 5.5 (m, 1H) ppm. $^{13}$C-NMR (CDCl$_3$) syn-isomer: δ 11.5 (t), 13.9 (q), 18.8 (d), 22.2 (d), 22.5 (q), 28.1 (d), 31.7 (t), 32.1 (t), 71.5 (d), 128.9 (d), 131.7 (d). $^{13}$C-NMR (CDCl$_3$) anti-isomer: δ 10.8 (t), 14.0 (q), 19.6 (d), 22.2 (d), 22.5 (q), 28.3 (d), 31.7 (t), 32.1 (t), 72.0 (d), 128.7 (d), 132.0 (d). syn-configuration assigned by GC retention time. MS (EI): m/z (%) 168 ([M]$^+$, 1), 150 ([M-H$_2$O]$^+$, 7), 113 (48), 95 (47), 82 (33), 81 (80), 68 (72), 67 (100), 57 (43), 55 (45), 54 (80), 45 (75), 43 (56), 41 (64). IR (film): 3340 (br, OH), 2958 (m), 2925 (m), 2871 (m), 2858 (m), 1455 (m), 1414 (w), 1366 (m), 1290 (w), 1180 (w), 1103 (m), 1076 (m), 1029 (m), 959 (s), 897 (m).

EXAMPLE 20

(cis)-1-hexyl-2-methylbicyclo[3.1.0]hexan-2-ol

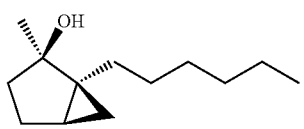

Methyl lithium 1.6 M in diethyl ether (4 ml, 7 mmol) is added dropwise to 2-hexylcyclopent-2-enone (Isojasmone B11) (1 g, 6 mmol) in diethylether (4 ml) at −78° C. At 0°-5° C. dibromomethane (3×0.6 ml, 24 mmol) and tert-butyl magnesium chloride 2M in diethyl ether (3×4 ml, 24 mmol) are added. Work-up after 18 h at 25° C. (as described in example 1) and bulb-to-bulb distillation gives 0.7 g (60%) of a colorless oil (cis/trans=93:7). $^1$H NMR (CDCl$_3$): δ 0.3 (m, 1H), 0.7 (m, 1H), 0.9 (t, 3H), 1.05 (m, 1H), 1.2-2 (15H), 1.3 (s, 3H) ppm. $^{13}$C-NMR (CDCl$_3$): δ 11.0 (t), 14.0 (q), 22.6 (t), 23.4 (d), 24.7 (t), 25.15 (q), 27.5 (t), 29.9 (t), 31.2 (t), 31.8 (t), 34.3 (s), 37.9 (t), 81.05 (s). cis-configuration assigned by COSY, HMBC, HSQC, NOESY in CDCl$_3$. MS (EI): m/z (%) 196 (M$^+$, 2), 181 ([M-15]$^+$, 14), 155 (24), 138 (15), 135 (27), 125 (32), 110 (34), 107 (38), 93 (92), 79 (50), 57 (14), 43 (100).

EXAMPLE 21

(cis)-5-isopropyl-2-methylbicyclo[3.1.0]hexan-2-ol

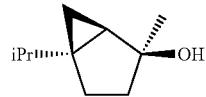

Prepared as described in Example 20 from 3-isopropylcyclopent-2-enone (V. Jurkauskas, J. P. Sadighi, S. L. Buchwald, Org. Lett. 5, 2417-2420, 2003), (0.5 g, 4 mmol), methyl lithium 1.6 M in diethyl ether (2.8 ml, 4.5 mmol), dibromomethane (2.8 g, 16 mmol) and tent-butyl-magnesium chloride 2M in diethyl ether (8 ml, 16 mmol) at 0°-10° C. Work-up after 6 h (as described in Example 1) and flash chromatography over silicagel (hexane/tert-butyl methyl ether 3:1) gave 0.23 g (45%) of a colorless oil. MS (EI): m/z (%) 196 (M$^+$, 5), 139 ([M-15]$^+$, 14), 136 ([M-18]$^+$, 29), 121 (38), 107 (12), 93 (100), 71 (60), 55 (34), 43 (85). NMR- and IR data identical with the ones described for cis-Sabinene Hydrate in the literature (D. Cheng, K. R. Knox, T. Cohen, J. Am. Chem. Soc. 122, 412-413, 2000).

EXAMPLE 22

(cis)-5-ethyl-1,2-dimethylbicyclo[3.1.0]hexan-2-ol

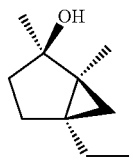

Prepared as described in Example 20 (System B) from 3-ethyl-2-methylcyclopent-2-enone (4 g, 32 mmol) (G. Berube, A. G. Fallix, Can. J. Chem. 69, 77-78, 1991), addition of methyl-lithium 1.6 M in diethyl ether (28 ml, 45 mmol) at −20° C., dibromomethane (2×8.4 g, 97 mmol) and tert-butyl magnesium chloride 2M in diethyl ether (2×24 ml, 97 mmol). Work-up after 18 h at 25° C. (as described in example 1) and bulb-to-bulb distillation gives 3 g (60%) of a waxy yellowish solid. $^1$H NMR (CDCl$_3$): δ-0.1 (d, 1H), 0.75 (d, 1H), 0.95 (t, 3H), 1.1 (s, 3H), 1.25 (s, 1H), 1.2-1.3 (1H), 1.3-1.4 (2H), 1.5-1.6 (2H), 1.7 (1H) ppm. $^{13}$C-NMR (CDCl$_3$): δ 11.4 (q), 12.7 (q), 18.4 (t), 24.9 (q), 25.8 (t), 28.5 (t), 32.35 (s), 34.6 (s), 36.5 (t), 81.3 (s). Cis-configuration determined by NMR-analysis in water-free DMSO. MS (EI): m/z (%) 154 (M$^+$, 1), 139 ([M-15]$^+$, 38), 136 ([M-18]$^+$, 67), 125 (37), 121 (27), 107 (86), 96 (59), 81 (100), 67 (30), 57 (42), 55 (36), 43 (86), 41 (40). IR (film): 3297 (br, OH), 2959 (s), 2859 (m), 1452 (s), 1365 (s), 1300 (m), 1199 (s), 1167 (m), 1115 (vs), 1062 (m), 970 (s), 938 (s), 926 (s).

EXAMPLE 23

(E)-2-(2-phenylcyclopropyl)propan-2-ol

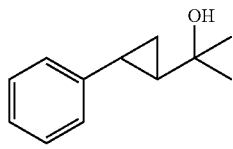

Methyl lithium 1.6 M in diethyl ether (27.5 ml, 44 mmol) was added dropwise to (E)-ethyl cinnamate (3 g, 19 mmol) in diethyl ether (15 ml) at −10° C. At 0°-5° C. dibromomethane (3×4.5 g, 75 mmol) and tert-butyl magnesium chloride 2M in diethyl ether (3×13 ml, 75 mmol) are added portionwise. Work-up after 18 h at 25° C. as described in Example 1 and bulb-to-bulb distillation under high vacuum gives 2.2 g (65%) of a colorless oil, whose analytical data are consistent with the ones described for this compound in the literature (e.g. by A. Mordini et al., *Tetrahedron* 61, 3349, 2005).

EXAMPLE 24

(trans)-2-(2-hexylcyclopropyl)propan-2-ol

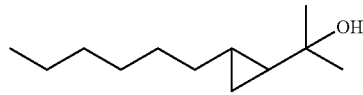

Prepared as described in Example 23 from methyl lithium 1.6 M in diethyl ether (7.4 ml, 12 mmol) and (E)-methyl non-2-enoate (Neofolione) (1 g, 6 mmol) in diethyl ether (10 ml) at −78° C., followed by dibromomethane (5×1 g, 30 mmol) and tert-butyl magnesium chloride 2M in diethyl ether (5×3 ml, 30 mmol) at 0°-5° C. Work-up after 18 h at 25° C. and bulb-to-bulb distillation under high vacuum gives 0.8 g (74%) of a colorless oil. $^1$H NMR (CDCl$_3$): δ 0.15 (m, 1H), 0.45 (m, 1H), 0.7 (2 m, 2H), 1.15 (s, 3H), 1.2 (s, 3H), 1.2-1.4 (7H) ppm. $^{13}$C-NMR (CDCl$_3$): δ 8.1 (t), 14.1 (q), 15.1 (d), 22.6 (t), 28.4 (q), 28.9 (q), 29.2 (t), 29.4 (t), 30.3 (d), 31.9 (t), 34.1 (t), 69.7 (s). MS (EI): m/z (%) 169 ([M-15]$^+$, 19), 151 (3), 123 (4), 110 (11), 109 (12), 97 (14), 95 (37), 72 (88), 71 (89), 43 (100). IR (film): 3377 (br, OH), 2960 (m), 2922 (s), 2853 (m), 1464 (m), 1367 (m), 1229 (w), 1145 (m), 944 (m), 915 (m).

EXAMPLE 25

((cis)-1-methyl-2-pentylcyclopropyl)methanol

2-Methyl-2-vinyl oxirane (1 g, 11 mmol) is added dropwise to n-butyl lithium 1.6 M in hexane (7 ml, 11 mmol) in diethyl ether (20 ml) at −78° C. After 1 h at −78° C. the solution is slowly warmed up to room temperature. Dibromomethane (7.7 g, 45 mmol) is added followed by dropwise addition of tert-butyl magnesium chloride (23 ml, 45 mmol) at 10°-20° C. After 24 h at 25° C. the mixture is poured upon 2M HCl. Extraction with tert-butyl methyl ether, washing of the organic phase with conc. NaHCO$_3$, conc. NaCl, drying over MgSO$_4$, filtration and evaporation of the solvents gives 2.3 g of a residue, which is purified by bulb-to-bulb distillation at 50° C./0.06 mbar giving 1.45 g (83%) of a colorless oil (cis/trans=85:15). $^1$H NMR (CDCl$_3$): δ 0.1 (m, 1H), 0.45 (m, 1H), 0.65 (m, 1H), 0.9 (t, 3H), 1.15 (s, 3H), 1.2-1.5 (8H), 3.5-3.6 (2 d, 2H) ppm. $^{13}$C-NMR (CDCl$_3$) cis-isomer: δ 14.0 (q), 17.6 (t), 22.0 (s), 22.6 (t), 22.7 (q), 25.1 (d), 29.2 (t), 29.9 (t), 31.7 (t), 67.5 (t). cis-configuration determined by $^{13}$C-NMR (CH$_2$O shift). $^{13}$C-NMR (CDCl$_3$) trans-isomer: δ 15.2 (q), 16.8̄ (t), 21.9 (s), 22.6 (t), 22.7 (q), 25.1 (d), 29.0 (t), 29.8 (t), 31.75 (t) 72.8 (t). MS (EI): m/z (%) 138 ([M-H$_2$O]$^+$, 1), 125 (1), 123 (1), 99 (33), 83 (47), 71 (42), 69 (44), 58 (98), 57 (87), 56 (68), 55 (100), 43 (51), 41 (63). IR (film): 3331 (br, OH), 2655 (m), 2924 (s), 2857 (m), 1465 (m), 1378 (w), 1198 (w), 1097 (w), 1028 (s), 966 (w), 920 (w), 973 (w), 725 (w).

EXAMPLE 26

((cis)-2-isobutyl-1-methylcyclopropyl)methanol

Prepared as described in Example 25 from 2-methyl-2-vinyl oxirane (1 g, 11 mmol), isopropyl-lithium 0.7 M in pentane (16 ml, 11 mmol), dibromomethane (7.7 g, 45 mmol) and tert-butyl magnesium chloride (23 ml, 45 mmol). Work-up and bulb-to-bulb distillation at 45° C./0.06 mbar gave 1.3 g (84%) of a colorless oil (cisltrans=75:25). $^1$H NMR (CDCl$_3$): δ 0.0 and 0.1 (2 m, 1H), 0.45 and 0.55 (2 m, 1H), 0.65 (1H), 0.9 (2 d, 6H), 1.05-1.15 (1H), 1.13 and 1.18 (2 s, 3H), 1.45 (1H), 1.65 (1H), 3.5-3.6 (2 d, 2H) ppm. $^{13}$C-NMR (CDCl$_3$) cis-isomer: δ 18.0 (t), 21.7 (s), 22.6 and 22.7 (2 q), 23.4 (d), 26.95 (q), 29.1 (d) 38.2 (t), 67.5 (t). cis-configuration determined by $^{13}$C-NMR (CH$_2$O shift). $^{13}$C-NMR (CDCl$_3$) trans-isomer: δ 16.9 (t), 21.8̄ (s), 22.5 and 22.7 (2 q), 23.4 (d), 29.0 (d), 29.4 (q), 38.0 (t), 72.8 (t). MS (EI): m/z (%) 124 ([M-H$_2$O]$^+$, 3), 111 (7), 109 (19), 85 (39), 71 (30), 69 (90), 58 (100), 57 (97), 56 (65), 56 (68), 55 (99), 43 (100), 41 (93). IR (film): 3335 (br, OH), 2953 (s), 2928 (m), 2902 (m), 2869 (m), 1465 (m), 1382 (m), 1366 (m), 1029 (s), 970 (w), 877 (w).

EXAMPLE 27

(1SR,3RS,4RS)-1-pentylspiro[2.7]decan-4-ol

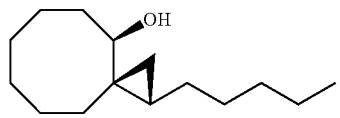 [SMILES: CCCCC[C@H]1C[C@]12CCCCCC[C@H]2O]

Prepared as described in Example 24 from 1-vinyl-9-oxabicyclo[6.1.0]nonane (J P Kokai S49-047345, Takasago Perfumery Co., Ltd.) (3 g, 18 mmol), n-butyl lithium 1.6 M in hexane (11 ml, 18 mmol), dibromomethane (12.5 g, 72 mmol)

and tent-butyl magnesium chloride (36 ml, 72 mmol). Workup and bulb-to-bulb distillation at 98° C./0.05 mbar gave 2.6 g (65%) of a colorless oil (dr=93:7). $^1$H NMR (CDCl$_3$): δ 0.3 (m, 1H), 0.5 (m, 1H), 0.8 (m, 1H), 0.8-1.1 and 1.2-2.4 (22H), 3.25 (1H) ppm. $^{13}$C-NMR (CDCl$_3$): δ 14.1 (q), 20.7 (t), 22.7 (t), 23.3 (t), 23.5 (t), 24.3 (d), 26.5 (t), 26.8 (t), 28.9 (t), 29.4 (s), 29.7 (t), 30.4 (t), 31.2 (t), 31.7 (t), 73.7 (d). cis-configuration assigned by COSY, HMBC, HSQC, NOESY in DMSO-D$_6$. MS (EI): m/z (%) 224 (M$^+$, 1), 206 ([M-18]$^+$, 10), 178 (4), 163 (5), 149 (12), 135 (22), 126 (24), 109 (22), 107 (24), 98 (58), 97 (33), 96 (80), 95 (46), 93 (54), 69 (41), 68 (42), 67 (84), 55 (100), 41 (80). IR (film): 3362 (br, OH), 2919 (s), 2852 (m), 1456 (m), 1364 (w), 1106 (w), 1029 (m), 989 (m), 811 (w), 741 (w), 726 (w).

The invention claimed is:

1. A method for the preparation of a compound of the formula

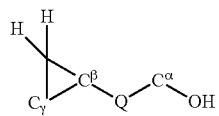

I comprising the generation of an alcoholate of the formula II

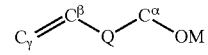

II and the subsequent cyclopropanation of this alcoholate with a reagent system selected from (A) magnesium metal and dibromomethane, and (B) dibromomethane and a tertiary Grignard reagent, the reaction being carried out in the presence of an ether solvent, C$^α$, C$^β$, C$^γ$ and Q being selected according to the possibilities (a) or and (b):

(a) C$^α$, C$^β$, C$^γ$ represent carbon atoms that may be protonated or substituted with up to a total of 5 substituents for all three carbon atoms, the substituents being selected from the group consisting of alkyl, alkenyl, cycloalkyl and cycloalkenyl groups; and Q represents a moiety selected from
  (i) a saturated or unsaturated carbon chain having from 1-6 carbon atoms, which carbon atoms are protonated or substituted, the substituents being selected from any of those of C$^α$, C$^β$, C$^γ$; and
  (ii) a single covalent bond joining C$^α$ and C$^β$;
and;
(b) C$^α$, C$^β$, C$^γ$ and all or part of Q together form a cycloalkyl or cycloalkenyl ring;
and
(c) M is an alkali metal, an alkaline earth metal, or an alkaline earth metal monohalide.

2. A method of preparation of a cyclopropyl carbinol, comprising the generation of an allylic alcoholate and the cyclopropanation of this allylic alcoholate with a reagent system selected from (A) magnesium metal and dibromomethane and (B) dibromomethane and a tertiary Grignard reagent, the reaction being carried out in the presence of an ether solvent.

3. A method according to claim 1, in which Q represents a single bond and the substitution of the allylic alcohol is selected from the following possibilities:
  (i) disubstituted in their α,γ- or β,γ-positions,
  (ii) trisubstituted in their α,β,γ-positions,
  (iii) tetrasubstituted in α,β,γ,γ-positions,
  (iv) pentasubstituted in their α,α,β,γ,γ-positions.

4. A method according to claim 1, in which the ether solvent is selected from the group consisting of THF, MTBE and diethyl ether.

5. A process according to claim 1, in which the tertiary Grignard reagent is tert-butyl-magnesium chloride or tert-amylmagnesium chloride.

6. A method for the preparation of (1-methyl-2-(1,2,2-trimethylbicyclo[3.1.0]-hex-3-ylmethyl)cyclopropyl)methanol comprising the step of: reacting 2-ethyl-4(2,2,3-trimethyl cyclopentyl-3-enyl)but-2-en-1-ol with a lithium reagent and then magnesium and dibromomethane in the presence of an ether solvent.

\* \* \* \* \*